United States Patent [19]

Scopes et al.

[11] Patent Number: 4,755,467

[45] Date of Patent: Jul. 5, 1988

[54] METHOD FOR THE PRODUCTION OF SORBITOL AND GLUCONATE

[75] Inventors: Robert K. Scopes, Hurstbridge; Peter L. Rogers, Northwood; Donald A. Leigh, Randwick, all of Australia

[73] Assignee: Unisearch Limited, Kensington, Australia

[21] Appl. No.: 802,178

[22] Filed: Nov. 26, 1985

[30] Foreign Application Priority Data

Jun. 3, 1985 [AU] Australia ............... PH0861

[51] Int. Cl.$^4$ ............ C12P 17/06; C12P 7/58
[52] U.S. Cl. ............ 435/125; 435/137; 435/158; 435/822
[58] Field of Search ............ 435/137, 105, 138, 136, 435/146, 189, 190, 197, 155, 94, 822, 253, 125, 158

[56] References Cited

U.S. PATENT DOCUMENTS

| | | | |
|---|---|---|---|
| 3,651,221 | 3/1972 | Conrad et al. | 435/190 |
| 4,352,885 | 10/1982 | Zeikus et al. | 435/189 |
| 4,403,034 | 9/1983 | Rogers et al. | 435/822 |
| 4,443,543 | 4/1984 | Rogers et al. | 435/822 |
| 4,443,544 | 4/1984 | Rogers et al. | 435/822 |

FOREIGN PATENT DOCUMENTS

| | | | |
|---|---|---|---|
| 0132557 | 8/1984 | European Pat. Off. | |
| 0142230 | 9/1984 | European Pat. Off. | 435/105 |
| 0142169 | 5/1985 | European Pat. Off. | 435/138 |
| 3326546 | 2/1985 | Fed. Rep. of Germany | 435/137 |

OTHER PUBLICATIONS

Viikari, Applied Microbiology and Biotechnology, vol. 20, pp. 118-123, 1984.
Barrow et al., Applied Microbiology and Biotechnology, vol. 20, pp. 225-232, 1984.
Viikari, Applied Microbiology and Biotechnology, vol. 20, pp. 252-255, 1984.
Leigh et al., Applied Microbiology and Biotechnology, vol. 20, pp. 413-415, 1984.

*Primary Examiner*—Charles F. Warren
*Assistant Examiner*—Elizabeth A. Hanley
*Attorney, Agent, or Firm*—Christie, Parker & Hale

[57] ABSTRACT

A method for the simultaneous production of sorbitol and either gluconolactone or gluconate from glucose and fructose. To this end to produce sorbitol and gluconolactone, glucose and fructose are reacted in the presence of a cell or cell-free extract of a bacteria, which contains the enzyme complex glucose/fructose transhydrogenase including the tightly bound co-factor(s), under condition whereby the further metabolism of gluconolactone is substantially prevented. In order to produce sorbitol and gluconate glucose and fructose are reacted in the presence of a cell or cell-free extract of a bacteria which contains an enzyme system comprising the enzyme complex glucose/fructose transhydrogenase including the tightly bound co-factor(s) and the enzyme gluconolactonase. This reaction is carried out under conditions whereby the metabolism of gluconate is substantially prevented. Preferably the bacteria used in this process is of the genus Zymomonas and most preferably of the species *Zymomonas mobilis*. The enzyme complex referred to as glucose/fructose transhydrogenase including the tightly bound co-factor(s) has been isolated in its pure form.

21 Claims, 2 Drawing Sheets

METHOD FOR THE PRODUCTION OF SORBITOL AND GLUCONATE

The present invention relates to a method for the simultaneous production of sorbitol and either gluconolactone or gluconic acid or its salts. As used in this application the term "gluconate" means gluconic acid and salts thereof.

It is known that sorbitol and gluconic acid or its salts can be produced by an enzymatic process from fructose and glucose using the enzymes sorbitol dehydrogenase and glucose dehydrogenase and adding the required co-factors (EP No. 0132557). In this process the glucose dehydrogenase is isolated from *Bacillus megaterium* and the sorbitol dehydrogenase from either sheep liver or *Bacillus subtilis*. This method, however, has the drawback that it is necessary to add co-factors in order to enable the enzymatic conversions to occur. This requirement of co-factors necessitates either the continuous addition of fresh co-factors or the use of an additional system (e.g. a redox system) to regenerate the co-factors. The addition of co-factors or of a system to regenerate the co-factors increases the cost and operational complexity of the process.

It is known that bacteria of the genus Zymomonas are efficient producers of ethanol from both glucose and fructose. It is also known however that under certain conditions these bacteria are not as efficient in the production of ethanol from sucrose which is a disaccharide hydrolyzing to glucose and fructose. It has been previously established that one of the reasons for the lower efficiency shown by these bacteria in the production of ethanol from sucrose is due to some of the sugar being utilised in the production of sorbitol rather than ethanol. The bacteria appear unable to utilise sorbitol so produced.

The present inventors have found that the sorbitol produced is derived preferentially from fructose rather than glucose and have further found that such sorbitol is produced at a faster rate when glucose concentration in the fermentation is in excess. They have further found that the process for sorbitol production involves oxidation of glucose to gluconolactone with a concomitant reduction of fructose to sorbitol, via an enzyme system which can be described as a glucose/fructose transhydrogenase.

It is believed that this enzyme system consists of a single enzyme which catalyses the transfer of hydrogen from glucose to fructose through a tightly bound non-dialysable co-factor which has been identified as NADP. The system being diagrammatically represented as:

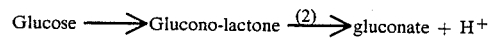

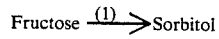

(1) = Glucose/fructose dehydrogenase
(2) = Gluconolactonase

The gluconate would, in a growing Zymomonas culture, typically be converted to 6-Phospho-gluconate and eventually to ethanol or some other end product. These conversions however require the presence of soluble, and dialysable, co-factors such as ADP/ATP, UDP/UTP, and NAD+/NADH and compounds including phosphate. Growing cell cultures would also involve a percentage of conversion of fructose to fructose-6-phosphate and then to glucose-6-phosphate which would also divert fructose, in the presence of low glucose concentrations, into the pathway leading to ethanol production.

The present invention relates to a process which will see the simultaneous production and accumulation of substantial amounts of sorbitol and either gluconolactone or gluconic acid or its salts.

The present invention consists in a method for the production of sorbitol and gluconolactone comprising reacting glucose and fructose in the presence of a bacteria which contains the enzyme complex glucose/fructose transhydrogenase including the tightly bound co-factor(s), or a cell-free extract of such a bacteria, containing the said enzyme complex, in which the bacteria, the cell-free extract or the reaction conditions is, or are, such that the further metabolism of gluconolactone is substantially prevented.

The present invention further consists in a method for the production of sorbitol and gluconic acid or salts thereof comprising reacting glucose and fructose in the presence of a bacteria which contains an enzyme system comprising the enzyme complex glucose/fructose transhydrogenase including the tightly bound co-factor(s) and the enzyme gluconolactonase, or a cell-free extract of such a bacteria, containing the said enzyme system, in which the bacteria, the cell-free extract or the reaction conditions is, or are, such that the further metabolism of gluconate is substantially prevented.

In yet a further aspect the present invention consists in a glucose/fructose transhydrogenase enzyme complex together with a tightly bound co-factor(s) isolated in its pure form from a bacteria.

The cells or cell-free extracts are preferably from bacteria of the genus Zymomonas and most preferably of the species *Zymomonas mobilis*. If cells are used the cells are preferably in the form of an immobilised culture. If cell extracts are used they may be extracts that have been prepared by bead-homogenizing cells, or by chemical lysis and separating debris by centrifugation.

In a still further embodiment of the invention the cells are merely non-growing cells that have been washed in phosphate-free buffer either with or without the cells having been made permeable. It is believed that this process so reduces the phosphate availability that the formation of 6-phospho-gluconate from the gluconate is prevented. This prevents the formation of substantial amounts of ethanol or other extraneous end products. Alternatively, a mutant strain lacking gluconokinase and/or gluconolactonase activity may be used.

The glucose and fructose may be added to the reaction medium separately though preferably in substantially equimolar amounts. In an alternative embodiment of the invention co-immobilised enzymes (or cells), or separate immobilized enzyme (or cell) bioreactors are incorporated in the system such that a sucrose solution or a glucose solution could be used as a sole substrate. In the case of sucrose an invertase enzyme would be used to produce an equimolar mix of glucose and fructose. In the case of glucose an isomerase would be used to convert the glucose to a glucose/fructose solution. In a still further embodiment of the invention strains of Zymomonas showing an invertase activity could be used to convert sucrose substrate into a glucose/fructose solution. Similarly, yeast or other cells with invertase activity could also be used. It is also within the ambit of this invention to utilise a variety of crude substrates such as starch which would require initial degradation to form glucose or dextrins.

The reaction may be carried out in a column reactor, tower type reactor, fluidised bed or a stirred tank reactor. The formation of gluconic acid may necessitate some form of pH control on the systems, e.g., a buffer such as carbonate may be used or alternatively a selected cation may be used to precipitate the corresponding gluconate salt. The addition of alkaline substances with a standard pH controller would also be possible.

The invention will now be described by way of example with reference to the accompanying Figures in which.

EXAMPLE 1

Figure 1:
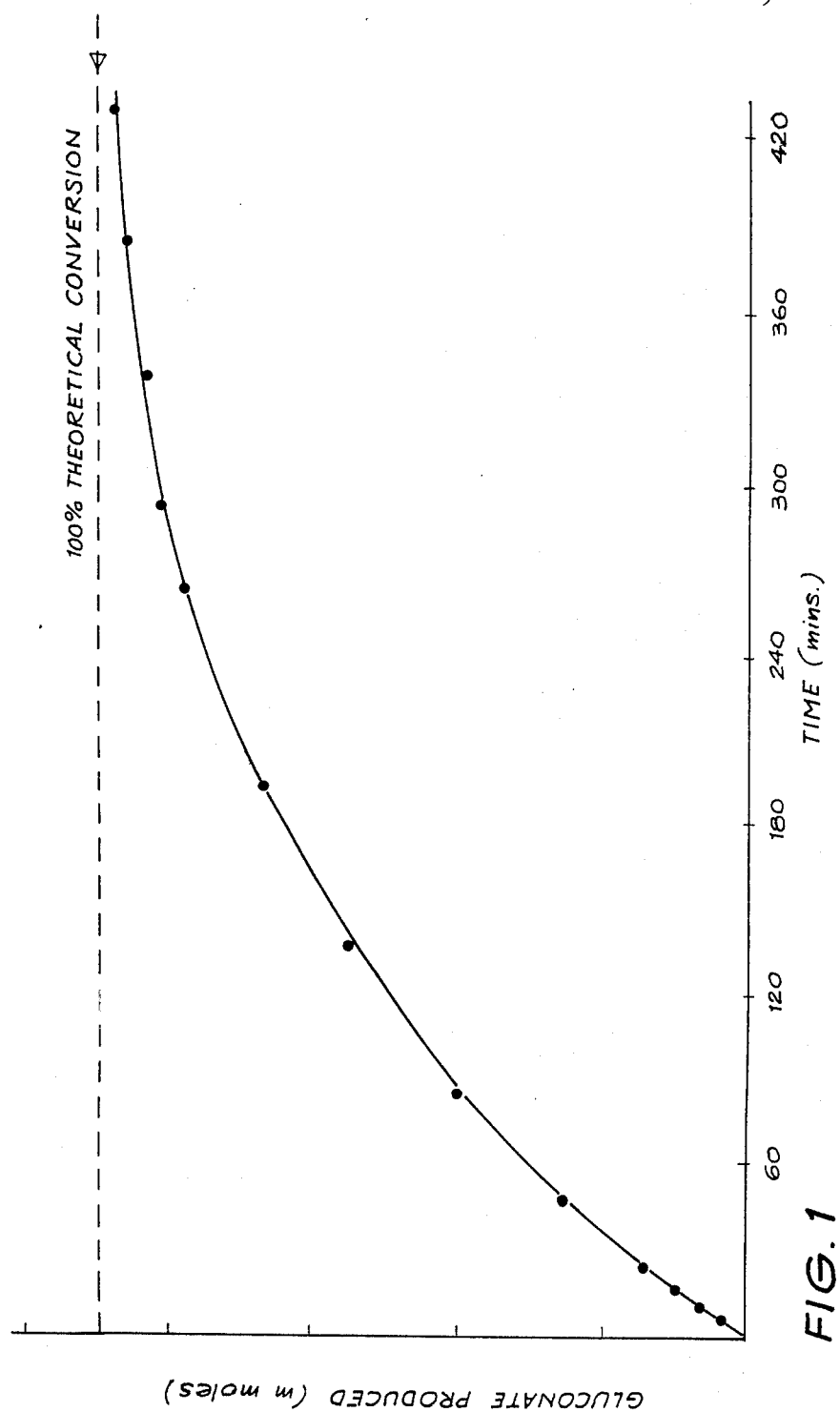
FIG. 1 shows the rate of gluconate production from glucose by permeabilized cells of Z. mobilis as a function of time.

Cell-free extracts of Z. mobilis ZM4 (ATCC 31821) were prepared by bead-homogenizing washed cells in pH 6.5 MES buffer +0.1% Nonidet P-40 for 2 minutes. The debris was separated by centrifugation (15,000 g for 15 min) and the supernatant was desalted on a Sephadex G25 column.

Cell-free incubations were carried out with desalted extract added to pH6.5 MES buffer with 100 to 200 mM of appropriate sugars. The samples were incubated for 2 hours at 30° C.

Sorbitol was measured using a sorbitol dehydrogenase (Bergmeyer et. al. in "Methods of Enzymatic Analysis" 2nd Ed. Bergmeyer (Ed.) Academic Press, New York, pp. 1323–1326, 1974). Gluconate was measured using gluconate kinase (Zachariou & Scopes, Biochemistry International, Vol. 10 pp 367–371, 1985) purified from Zymomonas, measuring ADP production with pyruvate kinase and lactate dehydrogenase.

Desalted crude cell-free enzyme preparations only produced detectable sorbitol when both glucose and fructose were added. Mannose and fructose together did not result in detectable sorbitol production nor did glucose or fructose separately. Formation of sorbitol was accompanied by an equivalent amount of gluconic acid, resulting in pH values 1 to 2 pH units below that of the control and precipitation of proteins. Mixtures not producing sorbitol did not alter in pH. None of the alternative electron acceptors to fructose, namely, acetaldehyde, acetoin, pyruvate, acetone or fructose 6-phosphate, were able to take the place of fructose.

Gas chromatographic analysis of supernatants of cell-free incubations confirmed the presence of sorbitol and the absence of mannitol.

More detailed investigation of the glucose-fructose transhydrogenase system indicated an optimum pH of between 5 and 7 and in particular near 6, a Km for glucose of 6 mM, and about 250 mM for fructose. The Vmax value matched or exceeded the in vivo rate of sorbitol formation.

EXAMPLE 2

Cells of Zymomonas mobilis growing in late exponential phase were harvested by centrifugation and washed with isotonic saline (8.5 g/l). The cells were treated with toluene (10% v/v in pH 7 buffer) in order to increase their permeability and remove soluble co-factors and high energy compounds necessary for complete conversion of glucose to ethanol. The cells were then prepared as a concentrated slurry (0.5 g wet weight) in a 3 ml solution containing 0.81 g glucose and 0.81 g fructose. The sugar concentrations corresponded to 1.5M each, and the absolute quantities could be expressed as 4.5 mmoles of both glucose and fructose.

Following addition of the toluene treated cells to the solution containing 1.5M glucose and 1.5M fructose, a rapid conversion of glucose to gluconate, and fructose to sorbitol occurred. The reaction temperature was maintained at 39° C. and the pH at 6.2 by the addition of 2M $Na_2CO_3$. The rate of production of gluconate as a function of time is shown in the FIG. 1. After 420 minutes, 4.4 moles of gluconate (estimated from alkali addition) and 4.3 mmoles of sorbitol (determined by standard enzymatic method) had been produced. This corresponds to at least 96% conversion in 420 mins with essentially equivalent amounts of both gluconate and sorbitol produced, indicating that both the glucose/-fructose transhydrogenase (and bound co-factor) and the gluconolactonase are active in the washed, toluene-treated cells. Removal of co-factors and energy compounds by washing and treatment with toluene has been effective in preventing the further conversion of gluconate to ethanol and/or other byproducts of catabolism.

EXAMPLE 3

A solution containing 2 ml of 1.2M (216 g/l) glucose and 1.2M (216 g/l) fructose was maintained at a temperature of 39° C. and pH=6.2, in the presence of 25 units of glucose/fructose transhydrogenase and 40 units of gluconolactonase purified from a strain of Zymomonas mobilis. Previous studies had shown that the pH optimum for the system was 6.0–6.2 and the temperature optimum approximately 40° C. The pH was maintained constant by the addition of 2M $Na_2CO_3$.

Figure 2:
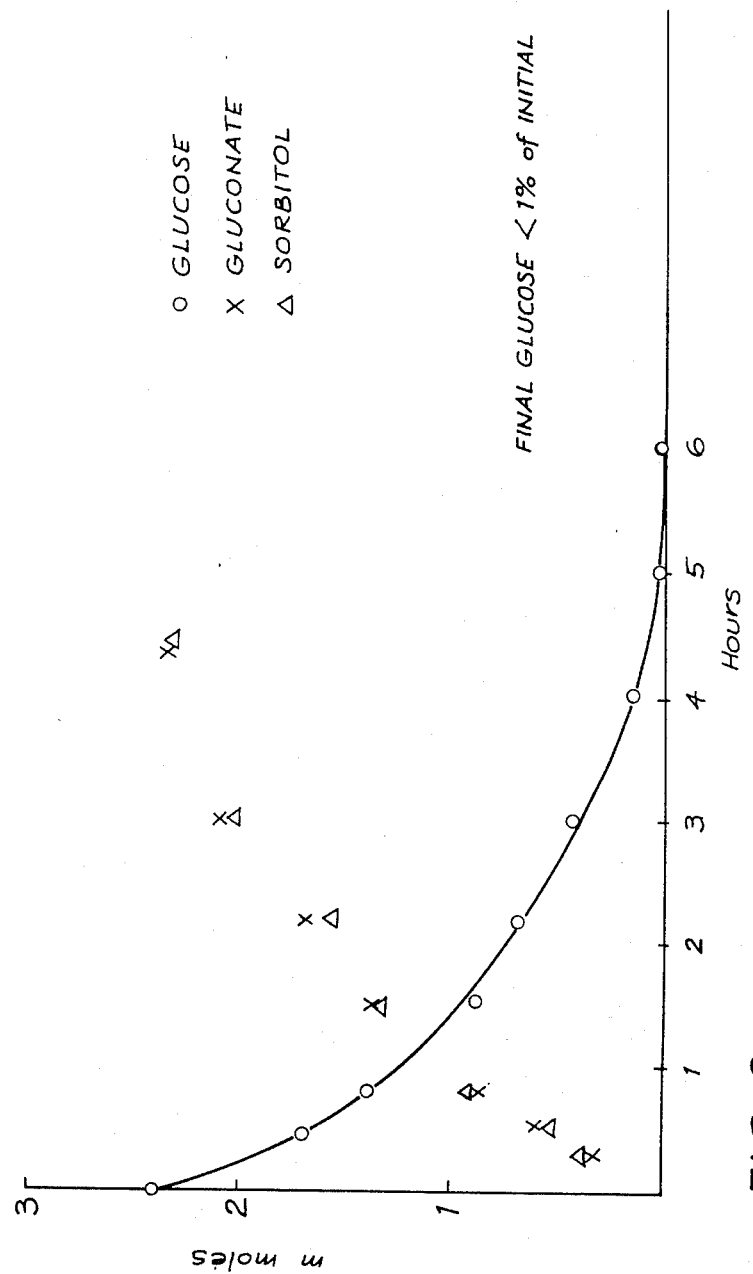
FIG. 2 shows the kinetics of the conversion of glucose to gluconate and of fructose to sorbitol by purified glucose/fructose transhydrogenase and gluconolactonase.

The kinetics of conversion of the glucose to gluconate (Na salt) and the fructose to sorbitol is shown in the accompanying FIG. 2.

Close to full conversion occurs after 5 h and 2.4 mmoles of glucose and fructose are converted to 2.35 mmoles of gluconate and sorbitol respectively. A 98% theoretical conversion has been achieved in that time at relatively high sugar concentrations indicating the efficiency and high conversion rate of the proposed process.

We claim:

1. A method for the production of sorbitol and gluconolactone comprising reacting glucose and fructose in the presence of a strain of Zymomonas mobilis which contains the enzyme complex glucose/fructose transhydrogenase including the tightly bound co-factor(s), or a cell-free extract of such a strain of Zymomonas mobilis, containing the said enzyme complex, in which the strain of Zymomonas mobilis, the cell-free extract or the reaction conditions are such that the further reaction of gluconolactone is substantially prevented.

2. A method for the production of sorbitol and gluconate comprising reacting glucose and fructose in the presence of a strain of Zymomonas mobilis which contains an enzyme system comprising the enzyme complex glucose/fructose transhydrogenase including the tightly bound cofactor(s) and the enzyme gluconolactonase, or a cell-free extract of such a strain of Zymomonas mobilis containing the said enzyme system, in which the strain of Zymomonas mobilis, the cell-free extract or the reaction conditions all such that the further reaction of gluconate is substantially prevented.

3. A method as claimed in claim 2 in which the strain of *Zymomonas mobilis* is in the form of permeabilized cells.

4. A method as claimed in claim 3 in which the permeabilized *Zymomonas mobilis* cells are in the form of an immobilized culture.

5. A method as claimed in claim 3 in which the permeabilized *Zymomonas mobilis* cells are phenotypically unable to metabolise gluconate.

6. A method as claimed in claim 2 in which the *Zymomonas mobilis* is not growing and is merely a cell suspension.

7. A method as claimed in claim 2 in which the glucose and fructose are added separately.

8. A method as claimed in claim 2 in which the glucose and fructose are formed in the presence of the strain of *Zymomonas mobilis* or extract by the action of an invertase enzyme on sucrose present in the reaction mixture.

9. A method as claimed in claim 8 in which the invertase is present within a microorganism or its cell-free extract.

10. A method as claimed in claim 9 in which the microorganism is the strain of *Zymomonas mobilis* possessing the glucose/fructose transhydrogenase enzyme complex including the tightly bound co-factor(s) and the gluconolactonase enzyme.

11. A method as claimed in claim 2 in which the glucose and fructose are formed in the presence of the strain of *Zymomonas mobilis* or extract by the action of an isomerase enzyme on glucose present in the reaction mixture.

12. A method as claimed in claim 11 in which the isomerase is present within a microorganism or its cell-free extract.

13. A method as claimed in claim 12 in which the microorganism is the bacterium possessing the glucose/fructose transhydrogenase enzyme complex including the tightly bound co-factor(s) and the gluconolactonase enzyme.

14. A method for the production of sorbitol and gluconolactone comprising reacting glucose and fructose in the presence of *Zymomonas mobilis* cells which have been washed in a phosphate-free buffer and which contain the enzyme complex glucose/fructose transhydrogenase including tightly bound co-factor(s) or in the presence of cell-free extract of such *Zymomonas mobilis* cells to thereby prevent further reaction of gluconolactone.

15. A method for the production of sorbitol and gluconate comprising reacting glucose and fructose in the presence of *Zymomonas mobilis* cells, which have been washed in a phosphate-free buffer and which contain the enzyme complex glucose/fructose transhydrogenase including tightly bound co-factor(s) and the enzyme gluconolactonase or in the presence of cell-free extract of such *Zymomonas mobilis* cells to thereby prevent further reaction of gluconate.

16. A method for the production of sorbitol and gluconolactone comprising reacting glucose and fructose in the presence of *Zymomonas mobilis* cells which contain the enzyme complex glucose/fructose transhydrogenase including tightly bound co-factor(s) and which are phenotypically unable to metabolize gluconolactone.

17. A method for the production of sorbitol and gluconate comprising reacting glucose and fructose in the presence of *Zymomonas mobilis* cells which contain the enzyme complex glucose/fructose transhydrogenase including tightly bound co-factor(s) and the enzyme gluconolactonase and which are phenotypically unable to metabolize gluconate.

18. A method as claimed in claim 1 in which the strain of *Zymomonas mobilis* is *Zymomonas mobilis* ZM4 (ATCC 31821).

19. A method as claimed in claim 2 in which the strain of *Zymomonas mobilis* is *Zymomonas mobilis* ZM4 (ATCC 31821).

20. A method for the production of sorbitol and gluconolactone comprising reacting glucose and fructose in the presence of the enzyme complex glucose/fructose transhydrogenase including the tightly bound co-factor(s) isolated from a strain of *Zymomonas mobilis*.

21. A method for the production of sorbitol and gluconate comprising reacting glucose and fructose in the presence of the enzyme complex glucose/fructose transhydrogenase including the tightly bound co-factor(s) and the enzyme gluconolactonase, both the enzyme complex and the gluconolactonase being isolated from a strain of *Zymomonas mobilis*.

* * * * *